US00PP26387P3

(12) United States Plant Patent

Ranney et al.

(10) Patent No.: US PP26,387 P3

(45) Date of Patent: Feb. 2, 2016

(54) *MISCANTHUS SINENSIS* GRASS NAMED 'NCMS1'

(50) Latin Name: *Miscanthus sinensis*
Varietal Denomination: NCMS1

(71) Applicant: North Carolina State University, Raleigh, NC (US)

(72) Inventors: Thomas G. Ranney, Raleigh, NC (US); Darren H. Touchell, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 125 days.

(21) Appl. No.: 13/999,797

(22) Filed: Mar. 21, 2014

(65) Prior Publication Data

US 2015/0271977 P1 Sep. 24, 2015

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Annette Para

(74) *Attorney, Agent, or Firm* — Myers Bigel Sibley & Sajovec, PA

(57) ABSTRACT

'NCMS1' is a new *Miscanthus sinensis* plant particularly distinguished by its triploid cytotype, low female fertility, and attractive form with showy inflorescences. 'NCMS1' provides an attractive and highly infertile alternative to diploid cultivars where reseeding and naturalization is a concern.

1 Drawing Sheet

Latin name of the genus and species: The Latin name of the novel plant variety disclosed herein is *Miscanthus sinensis.*

Varietal denomination: The inventive variety of *Miscanthus sinensis* disclosed herein has been given the varietal denomination 'NCMS1.'

BACKGROUND OF THE INVENTION

The present invention comprises a new and distinct cultivar of *miscanthus*, botanically known as *Miscanthus sinensis*, and hereinafter referred to by the cultivar name 'NCMS1'. This new *miscanthus* was developed and selected at North Carolina State University, Mills River, N.C. 'NCMS1' is a triploid produced from a controlled pollination. The female parent was an artificially induced tetraploid hybrid between *Miscanthus sinensis* 'Strictus' (not patented) and *Miscanthus sinenesis* 'Variegatus' (not patented). The male parent was a diploid *Miscanthus sinensis* 'Zebrinus' (not patented).

'NCMS1' was first established in vitro in 2007 through embryo rescue techniques and has been asexually reproduced through micropropagation and division at the North Carolina State University, Mountain Horticultural Crops Research Station, Mills River, N.C. over a 7 year period. 'NCMS1' has been evaluated in the field and containers for 6 years. 'NCMS1' can be propagated through micropropagation or division and has been found to retain its distinctive characteristics through successive asexual propagations.

SUMMARY OF THE INVENTION

The following traits have been repeatedly observed and are distinguishing characteristics of this new cultivar when grown under normal horticultural practices at North Carolina State University, Mountain Horticultural Crops Research Station, Mills River, N.C.

1. 'NCMS1' is a triploid *Miscanthus sinensis* with a 2C genome size of approximately 5.9 pg.
2. 'NCMS1' is highly infertile and has greatly reduced (99.3%) overall fertility (% seed set×% germination/100) compared to diploid *Miscanthus sinenesis* 'Zebrinus'.
3. 'NCMS1' has rigid upright culms and cascading leaf blades resulting in an attractive form with showy inflorescences.

DESCRIPTION OF THE PHOTOGRAPHS

The new *miscanthus* plant, 'NCMS1,' is illustrated by the accompanying photograph which shows the plant's form, foliage and inflorescences. The colors shown are as true as can be reasonably obtained by conventional photographic procedures. Colors in the photographs may differ slightly from the color values cited in the detailed botanical description, which accurately describe the colors of the new *Miscanthus sinensis*. The photographs were taken in Mills River, N.C.

FIG. 1 shows a 4-year-old plant growing in landscape conditions in Mills River, N.C. in August, 2012.

DETAILED BOTANICAL DESCRIPTION

The following is a detailed description of the botanical characteristics of the new and distinct variety of *Miscanthus sinensis* plant known by the denomination 'NCMS1'. The detailed description was taken on four-year old plants grown under landscape conditions in Mills River, N.C. in the summer and fall of 2012. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Botanical classification:

*Botanical name.*—*Miscanthus sinensis.*

*Common name.*—Maiden grass.

*Variety name.*—'NCMS1'.

*Parentage.*—Female parent: Tetraploid hybrid (Accession, H2008-024-001) of *Miscanthus sinensis* 'Strictus' ×*Miscanthus sinensis* 'Variegatus'. Male parent: *Miscanthus sinensis* 'Zebrinus' (Accession, 2004-200).

General description:

*Blooming period.*—Late August through early September in Mills River, N.C.

*Plant habit.*—Clump forming ornamental grass, rigid upright culms and cascading leaf blades, vase-shaped form.

*Height and spread.*—Reaches a height, including inflorescences, of 2.4-2.8 M (foliage approximately 1.8 M high), spread at base approximately 0.9 M, foliage cascading to approximately 0.9 M in diameter in 3 years.

*Cold hardiness.*—At least USDA zone 6; testing has not been completed in colder zones.

*Culture.*—Optimal growth in fertile moist soil in full sun.

*Disease and pests.*—No significant disease or insect pests have been observed.

*Root description.*—Fibrous.

*Propagation.*—Propagated through culm division and micropropagation.

Culm (stem) description:

*General.*—Cylindrical, smooth, partially enclosed by leaf sheaths.

*Culm aspect.*—Erect and rigid, all extending from ground, non-cascading.

*Culm color.*—146 B.

*Culm size.*—Up to 4.0 to 7.5 mm wide, 1.2-1.8 M high in mature plants.

*Culm surface.*—Glabrous.

*Internode length.*—11.5 to 24 cm.

*Ligule.*—Membraneous about 3-4 mm in width.

Foliage description:

*Leaf shape.*—Linear. Leaf division: Simple. Leaf base: Sheathed.

*Leaf apex.*—Acute. Leaf aspect: Emerging leaves are erect and diverge from the sheath at an angle in the range of 30° to 45° from the center of the culm. Leaves are concave with respect to the culm.

*Leaf venation.*—Parallel, mid rib is recessed on upper surface and extends through entire leaf and is white (155B to 155C).

*Leaf margins.*—Entire, crenulate with small membraneous serrations.

*Leaf persistence.*—Leaves desiccate after freezing, but remain attached to the culm through winter.

*Leaf attachment.*—Sheathed. Leaf blade extends out from the culm at a ligule.

*Leaf size.*—Up to 100 cm in length and 24 mm in width, tapering to a point at the apex.

*Leaf surface.*—Glabrous on the adaxial (upper) and abaxial (lower) surface with ribbing protruding on the abaxial surface parallel to the mid rib.

*Leaf number.*—About 8 to 10 per culm on a mature plant.

*Leaf arrangement.*—Alternate, 2 ranked.

*Leaf color.*—Uniformly green, 137 B on the adaxial (upper) surface and 139 A on the abaxial (lower) surface.

Flower description:

*General description.*—Panicle terminating from each culm in late-August to early September, composed of up to 36 cascading racemes at anthesis.

*Lasting of the infloresence.*—Panicles are persistent throughout winter.

*Fragrance.*—None.

*Panicle size.*—Average size 31 cm in length and 4 to 6 cm in width.

*Panicle color.*—Emerges 162 A and turns a beige during dormancy 161 D.

*Raceme (spike) description.*—Racemes up to 22 cm long, up to 36 Racemes (spikes) per panicle.

*Spikelet description.*—Equal glumes surround a shorter hyaline lemma, smaller hyaline palae, awn extending 6 mm beyond spikelet, approximately 60 spikelets per raceme, arranged in two pairs unequally pedillate. Spikelet size: About 6 mm in length and 1 mm in width (excluding hairs). Spikelet hairs: Emerging from the base, very fine, average of 7 mm in length.

Reproductive organs:

*Androceum.*—Anthers; 3, 2 mm in length and <0.5 mm in width, 165 A in color, attached to spikelet by a thin filament approximately 1 mm. Pollen present.

*Gynoecium.*—Pistil 1; 2 plumose stigmas, 2 mm in length and <0.5 mm in width, N186A in color short filamentous styles. Ovary; 1 locule, superior.

Fertility: In a replicated study (See, Rounsaville et al., 2011), 'NCMS1' (H2008-091-004) had greatly reduced female fertility compared with the diploid control, 'Zebrinus' (Table 1).

TABLE 1

Comparison of female fertility between the diploid cultivar 'Zebrinus' and the triploid cultivar 'NCMS1'.

| Cultivar | Seed set (%) | Germination (%) | Overall fertility (%) | Relative fertility (%) |
|---|---|---|---|---|
| 'Zebrinus' | 74.4 | 73.4 | 55.3 | 100.0 |
| 'NCMS1' | 0.7 | 56.3 | 0.4 | 0.7 |

Where seed set (%) = (number of seeds/number of florets) × 100; germination (%) = (seeds germinated/total seeds) × 100; overall fertility = seed set (%) × germination (%)/100; and relative fertility = [overall fertility/55.3 (control value)] × 100.

Furthermore, the limited progeny derived from open-pollinated 'NCMS1' plants were aneuploids with 2C genome sizes intermediate between diploids and triploids. As such, 'NCMS1' provides an attractive and highly infertile alternative to diploid cultivars where reseeding and naturalization is a concern.

Comparison with other cultivars: 'NCMS1' is distinguished from its parents and other cultivars as it is an autotriploid of *Miscanthus sinensis* and has reduced fertility (Table 2). In comparison to its parents, 'NCMS1' does not have any vertical or horizontal banding on its leaves. 'NCMS1' is a triploid *Miscanthus sinensis* compared to *M.×giganteus* which is a highly infertile triploid between *M. sacchariflorus* and *M. sinensis*. 'NCMS1' is not as tall as *M.×giganteus*.

TABLE 2

Comparison of 'NCMS1' with other *Miscanthus* cultivars.

| Trait | Cultivar | | | | |
|---|---|---|---|---|---|
| | 'NCMS1' | 'Variegatus' | 'Strictus' | 'Zebrinus' | [x]gigan-teus |
| Cytotype | 3x | 2x | 2x | 2x | 3x |
| 2C relative genome size (pg) | 5.9 | 3.9 | 4.1 | 4.1 | 5.7 |
| Fertility | highly infertile | fertile | fertile | fertile | highly infertile |
| Plant size | | | | | |
| Foliage height | 1.8M | 1.8M | 1.5M | 1.5M | 2.7-3.0M |
| Flower height | 2.7M | 2.7M | 2.4M | 2.4M | 3.7M |

TABLE 2-continued

Comparison of 'NCMS1' with other *Miscanthus* cultivars.

| Trait | Cultivar | | | | |
|---|---|---|---|---|---|
| | 'NCMS1' | 'Variegatus' | 'Strictus' | 'Zebrinus' | [x]gigan-teus |
| Foliage color | Green | Vertically banded | Horizontal banding | Horizontal banding | Green |
| Green | 137B | 137A | 147A | 137A-137B | 146A |
| Band | NA | 5D | 4B | 4B | NA |

Citations:
Rounsaville, T. J., D. H. Touchell, and T. G. Ranney. 2011. Fertility and reproductive pathways in diploid and triploid *Miscanthus sinensis*. *Hortscience* 46(10):1353-1357.

What is claimed is:

1. A new and distinct cultivar of *Miscanthus sinensis* named 'NCMS1', substantially as illustrated and described herein.

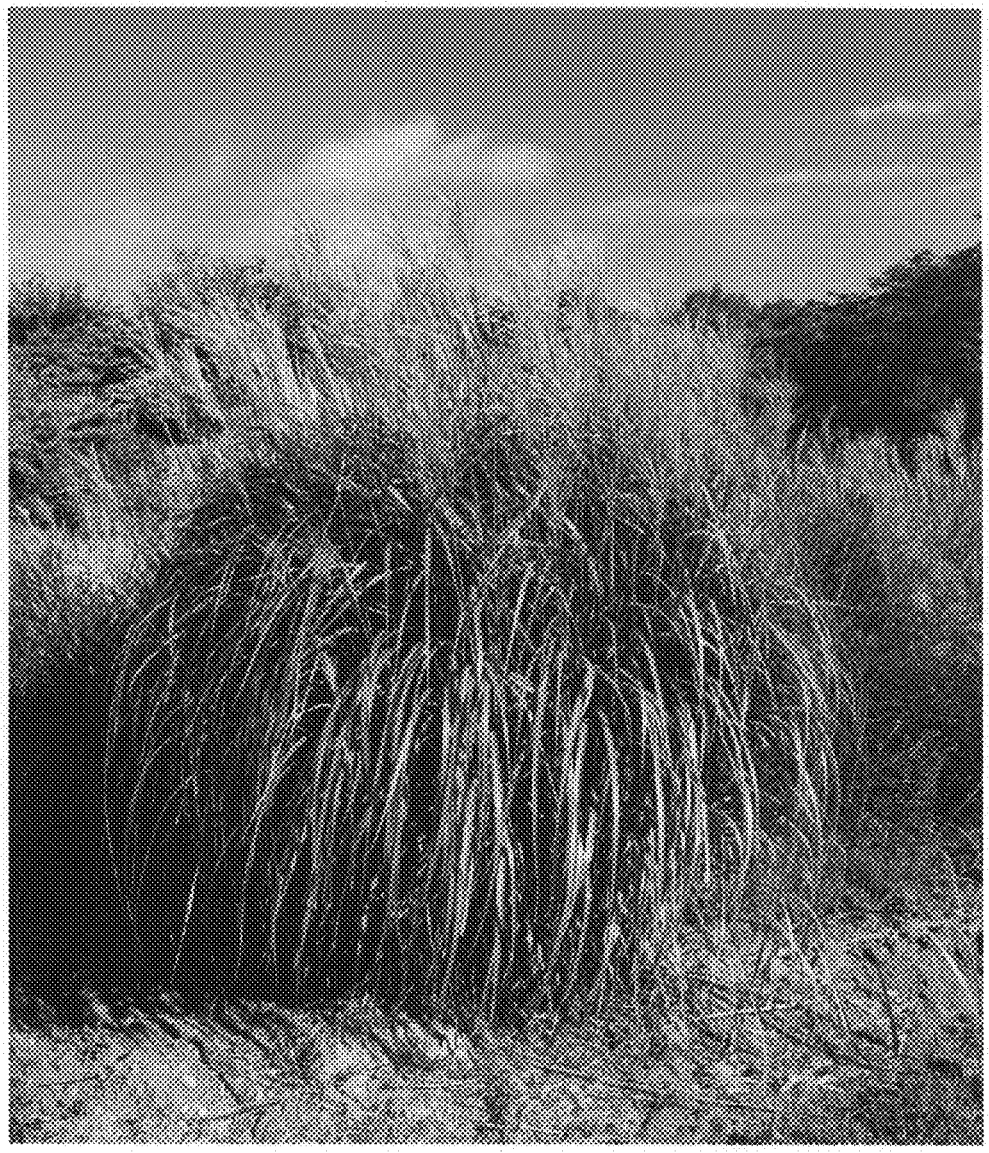

* * * * *